United States Patent [19]

Bringhurst et al.

[11] Plant 4,538

[45] May 27, 1980

[54] STRAWBERRY PLANT

[75] Inventors: Royce S. Bringhurst, Davis; Victor Voth, Santa Ana, both of Calif.

[73] Assignee: The Regents of the University of California, Berkeley, Calif.

[21] Appl. No.: 953,814

[22] Filed: Oct. 23, 1978

[51] Int. Cl.[2] ..... A01H 5/00

[52] U.S. Cl. ..... Plt./49

[58] Field of Search ..... Plt./48, 49

*Primary Examiner*—Robert E. Bagwill
*Assistant Examiner*—James R. Feyrer
*Attorney, Agent, or Firm*—Townsend and Townsend

[57] ABSTRACT

A new and distinct variety of strawberry plant of a short-day type characterized by best performance in the Watsonville, Calif., area where yield is nearly as much as the heavy yielding cultivars Tioga, Tufts and Aiko on summer plantings and in winter plantings with yield about 80% that of Tufts. Fruit is particularly attractive and firm. Fruit shape is medium to long conic with primaries frequently wedged and slight necked and its skin nearly always smooth and glossy. Fruit is firmer and more durable than Aiko, Tioga or Tufts when grown in Watsonville and somewhat larger than Tufts. Fruit flavor is equal to or better than the best important California cultivars and shipping characteristics are excellent.

3 Drawing Figures

This invention relates to a new and distinctive short-day type strawberry cultivar designated as C45 which is the result of a cross between Cal 63.7-101 (not patented) and "Sequoia", U.S. Plt. Pat. No. 3,178.

C45 first fruited at the University of California, South Coast Field Station, Santa Ana in 1973 where it was selected and designated originally as Cal 71.101-611.

C45 has since been tested with favorable results and asexually reproduced by runners at various University of California Field Stations and facilities and has also been favorably tested in a limited way in representative growers' fields under strict control. Meristem originated virus negative stock for asexual reproduction is under development at the University of California.

FIG. 1 of the accompanying photographic color reproductions shows typical growth, flowering and fruiting characteristics of C45 in a summer planting at Watsonville in mid-July.

Figure 1:
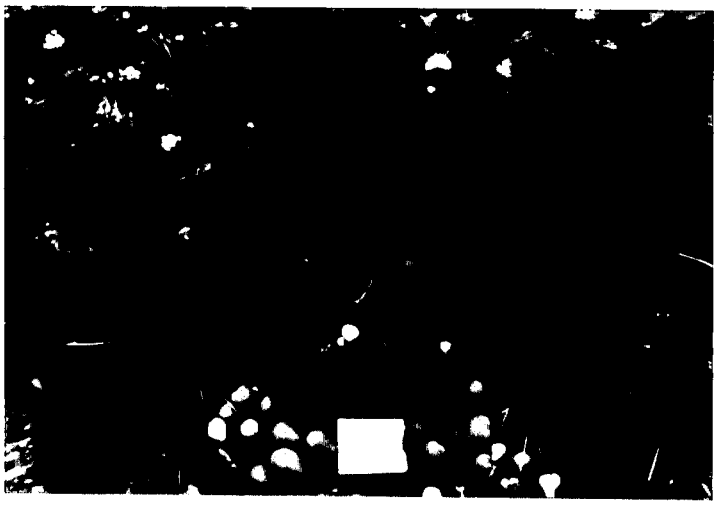
Figure 2:
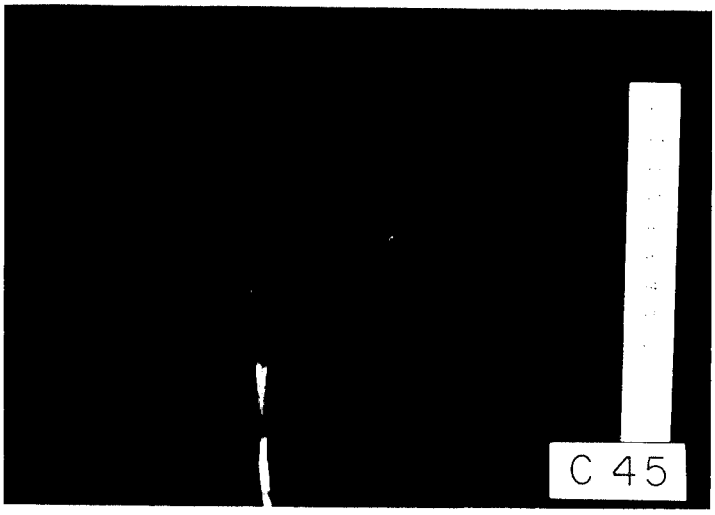
FIG. 2 shows a typical mid-summer mature leaf from a winter planted plant.
Figure 3:
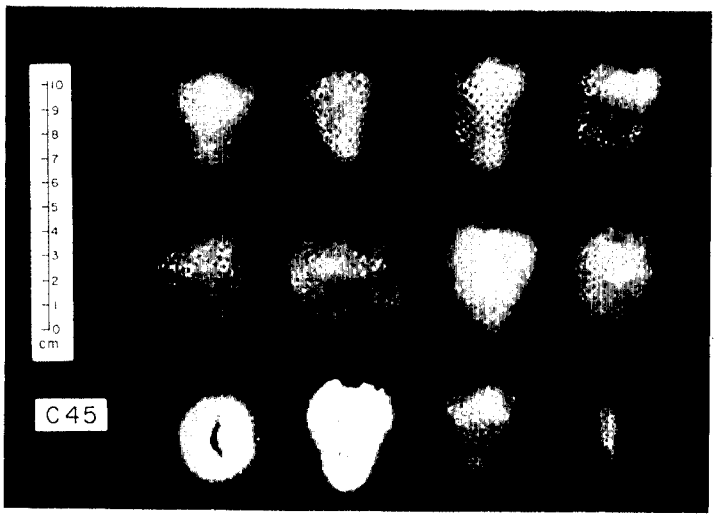
FIG. 3 shows representative mid-season fruit of C45 with longitudinal and cross section views.

C45 has performed best in the Watsonville area where it may yield almost as much as the heavy yielding California cultivars "Tioga" (not patented), "Tufts" (U.S. Plt. Pat. No. 3,561) or "Aiko" (U.S. Plt. Pat. No. 3,981) on summer plantings under favorable conditions. It has yielded only about 80% as much as "Tufts" in winter plantings in the same area but the fruit is particularly attractive and firm.

The distinctive characteristics of this new strawberry cultivar described in detail below were observed upon its discovery and/or through the test period.

DESCRIPTION

*Plants and foliage.*—C45 plants are erect in growth habit, similar to "Aiko"; medium sized, somewhat larger than "Aiko" and slightly smaller than "Tufts" or "Tioga". Bract leaves occur on about 50% and 10% of the petioles of plants of winter and summer plantings, respectively; much less than "Tufts" or "Tioga" and about the same as "Aiko". Leaflets of C45 are about the same size as those of "Tioga" and "Tufts" larger than "Aiko". They are about as dark colored as those of "Tioga", but slightly less yellow roughly 5 GY 4/3 vs. 2.5 GY 4/3 for "Tioga" (Munsell Color System — Nickerson Color Fan). The leaflets have about the same number of serrations as those of "Aiko" and "Tioga" (av of ±10/half blade) but less than "Tufts" (av of ±12/half blade) as averaged over half blades of the 3 leaflets on mid-season mature leaves at Watsonville. The plants are vigorous and C45 is a prolific runner maker in the nursery.

*Isozymes in leaf extracts.*—Phosphoglucose isomerase (PGI): C45 gave a 5 banded pattern similar to that of "Aiko", 30/35 35/35 35/35 35/40 mm, different than the "Tioga" single band, or the "Tufts" slow 3 banded patterns (Scandalios. 1969. Biochem. Genet. 3:37–79).

*Flowering and flowers.*—C45 is a standard short-day type that commences flowering about with "Tufts" in coastal Central California. Inflorescences are somewhat shorter than those of "Tufts" but longer than those of "Aiko" and much longer than those of "Tioga". The flowers are highly self fertile with ample pollen throughout the season.

*Fruit and fruiting.*—C45 has medium to long conic fruit, almost always smooth, usually somewhat hollow centered and the primaries are frequently wedged in varying degrees, much of it with a slight neck. The fruit skin color of C45 is distinctly redder and considerably darker than that of "Tioga", about 5 R 4/12 vs. 7.5 R 4/11, respectively (ibid). The finish is particularly glossy and attractive but with a tendency to light shoulder color early in the season. The flesh color is about the same as the skin ranging to a lighter center. The calyx is large and attractive, tending to be reflexed. The achene position is normally about flush with the fruit surface similar to "Tioga." The fruit is firmer and more durable than that of "Aiko", "Tioga" or "Tufts", giving penetrometer readings of ±7.6 vs. ±6.7 for the three cultivars at Watsonville. The fruit of C45 also has averaged somewhat larger in size than that of "Tufts", in most tests, typically about ±23 g/fr. vs. ±21 for "Tufts".

*Fruit quality.*—Ascorbic acid: C45 averaged ±54 mg/100 g of fresh fruit, greater than "Tioga" (±40) or "Tufts" (±45) and less than "Aiko" (±60) as tested by the method of Loeffler and Ponting. 1942. J. Indust. and Engin. Chem. 14:846. Soluble solids: C45 averaged ±8.4% not significantly different from "Aiko", "Tioga" or "Tufts" according to our measurements on mid-summer Watsonville fruit. The flavor of C45 is equal to or better than that of the best important California cultivars in our opinion. Many have judged it exceptionally good. As a shipping fruit, it is outstanding and it should be very adequate for processing.

We claim:

1. The new and distinct variety of strawberry plant herein described and illustrated, and identified by the characteristics enumerated above.

* * * * *